US010130556B2

United States Patent
Fujita

(10) Patent No.: US 10,130,556 B2
(45) Date of Patent: Nov. 20, 2018

(54) SKIN STRETCHING TAPE AND METHOD OF ALLEVIATING PAIN

(71) Applicant: Makoto Fujita, Osaka (JP)

(72) Inventor: Makoto Fujita, Osaka (JP)

(*) Notice: Subject to any disclaimer, the term of this patent is extended or adjusted under 35 U.S.C. 154(b) by 279 days.

(21) Appl. No.: 15/053,129

(22) Filed: Feb. 25, 2016

(65) Prior Publication Data

US 2016/0166467 A1    Jun. 16, 2016

Related U.S. Application Data

(63) Continuation-in-part of application No. 14/574,446, filed on Dec. 18, 2014.

(30) Foreign Application Priority Data

Aug. 11, 2014 (JP) .................................. 2014-163692
Aug. 28, 2015 (JP) .................................. 2015-169425

(51) Int. Cl.
| | |
|---|---|
| *A61F 5/37* | (2006.01) |
| *A61H 39/04* | (2006.01) |
| *A61H 37/00* | (2006.01) |
| *A61H 39/08* | (2006.01) |
| *A61F 5/01* | (2006.01) |
| *A61F 5/30* | (2006.01) |

(52) U.S. Cl.
CPC ............ *A61H 39/04* (2013.01); *A61F 5/0102* (2013.01); *A61F 5/30* (2013.01); *A61F 5/37* (2013.01); *A61H 37/00* (2013.01); *A61H 39/08* (2013.01); *A61H 2201/165* (2013.01); *A61H 2201/1654* (2013.01)

(58) Field of Classification Search
CPC .. A61F 13/00038; A61F 13/02; A61F 13/023; A61F 13/0233; A61F 13/0236; A61F 13/0243; A61F 13/0269; A61F 13/0273
See application file for complete search history.

(56) References Cited

U.S. PATENT DOCUMENTS

| | | | | |
|---|---|---|---|---|
| 5,116,675 | A * | 5/1992 | Nash-Morgan | ....... A61F 13/023 428/343 |
| 6,120,470 | A * | 9/2000 | Bodenschatz | ......... A61F 13/102 602/20 |
| 2016/0038372 | A1 * | 2/2016 | Fujita | ..................... A61H 39/04 606/204 |

OTHER PUBLICATIONS

Makoto Fujita. Pain Free. Book. Osaka, Japan: Design Egg, May 2015, pp. 19, pp. 29-30, pp. 32-33.

(Continued)

*Primary Examiner* — Todd Scherbel
(74) *Attorney, Agent, or Firm* — Kubotera & Associates, LLC

(57) ABSTRACT

A skin stretching tape includes a first sheet member formed of a non-stretchable material, and having a first backside surface with an adhesive compound applied thereto; and a second sheet member formed of a stretchable material in a band shape, and having a second backside surface with an adhesive compound applied thereto. The first sheet member is attached to the second backside surface at one end portion of the second sheet member. The second sheet member has a length in a longitudinal direction thereof greater than twice of that of the first sheet member. The first sheet member may have a circular shape. Further, the second sheet member may have the length in the longitudinal direction thereof three times to five times of that of the first sheet member.

8 Claims, 12 Drawing Sheets

(56) References Cited

OTHER PUBLICATIONS

Makoto Fujita. Pain Free. http://www.painfree-jp.com/ : Aug. 18, 2015.

* cited by examiner

SKIN STRETCHING TAPE AND METHOD OF ALLEVIATING PAIN

CROSS-REFERENCE TO RELATED APPLICATIONS

This is a continuation-in-part application of a prior, application Ser. No. 14/574,446, filed on Dec. 18, 2014, pending, which claims priority of Japanese Patent Application No. 2015-169425, filed on Aug. 28, 2015 and Japanese Patent Application No. 2014-163692, filed on Aug. 11, 2014.

BACKGROUND OF THE INVENTION AND RELATED ART STATEMENT

The present invention relates to a skin stretching tape for stretching a skin in one direction, and a method of alleviating an aching pain such as a muscle ache and the like using the skin stretching tape.

In general, an aching pain such as a back pain occurs under various circumstances regardless of the nature of the aching pain, i.e., a chronic pain or an acute pain. In many cases, such an aching pain tends to be felt as an excessive tension near a skin, in particular, a specific portion of a muscle. Usually, such a specific portion of the muscle having the excessive tension is pressed with a finger and the like, so that the aching pain becomes more prominent locally, thereby making it possible to easily detect a location of the aching pain.

In order to alleviate the aching pain, a massage, a packing sheet, and a local taping have been generally applied to an affected area where the aching pain occurs. When the massage is applied to the muscle, it is possible to promote a blood flow in the muscle, so that the muscle can be recuperated more rapidly. However, it is difficult to apply the massage to an affected area for a long period of time. Accordingly, even when the tension in the muscle is moderated, and the aching pain is alleviated upon applying the massage, it is still difficult to obtain a prolong effect of the massage. When the muscle ache is still in an early stage, the packing sheet may be applied to the affected area to cool or warm a muscle, so that the muscle can be recuperated more rapidly. It is possible to maintain the affected area with the packing sheet applied thereto for a relatively long period of time, so that it is possible to obtain a prolong effect thereof. However, it is evitable that an effect of an ingredient contained in the packing sheet declines with time, so that the effect of the packing sheet also declines with time.

As compared with the muscle pain alleviation remedies described above, in the local taping method, a band-shaped long tape is affixed to a skin above the muscle at the affected area along a specific direction according to an extending direction the muscle, so that a movement of the muscle is supported as well as the blood flow in the muscle is promoted through stretching the skin. An effect of the local taping method does not decline within a short period of time, so that it is possible to maintain a prolonged effect thereof for a relatively long period of time.

In the local taping method, however, the tape is applied over an entire portion of the muscle around the affected area. Accordingly, when the muscle pain is limited to a small area, it is difficult to effectively apply the tape at the small area. Further, it is necessary to affix the tape in different ways depending on an area, thereby making it necessary to attain experience for a practitioner to affix the tape properly.

In view of the problems described above, an object of the present invention is to provide a novel method of alleviating the muscle pain using a skin stretching tape. According to the present invention, even if the muscle pain is limited to a small area, it is possible to easily affix the skin stretching tape only at an affected area without extensive experience. Further, another object of the present invention is to provide the skin stretching tape to be used in the method.

Further objects and advantages of the invention will be apparent from the following description of the invention.

SUMMARY OF THE INVENTION

In order to attain the objects described above, according to a first aspect of the present invention, a skin stretching tape includes a first sheet member and a second sheet member. The first sheet member is formed of a non-stretchable material, and has a first backside surface with an adhesive compound applied thereto. The second sheet member is formed of a stretchable material in a band shape, and has a second backside surface with an adhesive compound applied thereto. The first sheet member is attached to the second backside surface at one end portion of the second sheet member. Further, the second sheet member has a length in a longitudinal direction thereof greater than twice of that of the first sheet member.

According to a second aspect of the present invention, in the skin stretching tape described above, it is preferred that the first sheet member may have a circular shape. Alternatively, the first sheet member may be formed in a shape having contact points with a circle that forms a polygonal shape when the shape is fitted in the circle. Further, the second sheet member may have the length in the longitudinal direction thereof three times to five times of that of the first sheet member.

According to a third aspect of the present invention, in the skin stretching tape described above, it is preferred that the second sheet member may have a first portion at the one end portion thereof where the first sheet member is attached and a second portion extending to the other end portion thereof where the first sheet member is not attached. The second portion has a width in a direction perpendicular to the longitudinal direction smaller than that of the first sheet member. In particular, it is preferred that the second portion has the width one third to a half of that of the first sheet member.

According to a fourth aspect of the present invention, in the skin stretching tape described above, it is preferred that the skin stretching tape may have an outer circumferential edge having no corner portion smaller than 180 degrees. Further, the skin stretching tape may include a release sheet member detachably attached to the first backside surface and the second backside surface with the adhesive compound applied thereto.

According to a fifth aspect of the present invention, a skin stretching tape includes a first sheet member and a second sheet member separated from the first sheet member in advance. A first front side surface of the first sheet member is attached to a backside surface of the second sheet member at one end portion thereof, so that the first sheet member is fixed to the second sheet member. Further, the one end portion of the second sheet member, to which the first sheet member is fixed, may be formed of a transparent material or a semi-transparent material.

According to a sixth aspect of the present invention, in the skin stretching tape described above, it is preferred that a reinforcement sheet is detachably attached to a second front side surface of the second sheet member substantially over a longitudinal direction thereof. The reinforcement sheet is formed of a material having a flexural strength greater than that of the second sheet member. Further, the reinforcement sheet is formed of a non-stretchable material, and is divided with a dividing line crossing the longitudinal direction thereof.

According to a seventh aspect of the present invention, the skin stretching tape may include a release sheet member disposed at a portion of the second sheet member with an adhesive compound applied thereto, so that the release sheet member covers the portion and detachably attached to the adhesive compound. Further, the release sheet member is divided with a dividing line crossing the longitudinal direction thereof at the other end portion of the second sheet member, to which the first sheet member is not fixed.

According to an eighth aspect of the present invention, a method of alleviating an aching pain uses the skin stretching tape described above and formed of the first sheet member and the second sheet member integrated with the first sheet member in advance. The method includes a first step of pushing a skin with a finger so that a location of a muscle where a large tension occurs is detected according to a degree of the aching pain or discomfort; a second step of detecting a direction in which the aching pain or discomfort is lessened through changing pushing directions in parallel to the skin while pushing the skin at the location detected in the first step; a third step of affixing the first backside surface of the first sheet member of the skin stretching tape to the skin at the location detected in the first step so that the other end portion of the second sheet member where the first sheet member is not attached is aligned with the direction detected in the second step; and a fourth step of affixing the second backside surface of the second sheet member to the skin after the other end portion of the second sheet member is stretched and extended in the longitudinal direction.

According to a ninth aspect of the present invention, a method of alleviating an aching pain uses the skin stretching tape described above and formed of the first sheet member and the second sheet member separated from the first sheet member in advance. The method includes a first step of pushing a skin with a finger so that a location of a muscle where a large tension occurs is detected according to a degree of the aching pain or discomfort; a second step of affixing the first sheet member of the skin stretching tape to the skin at the location detected in the first step; a third step of detecting a direction in which the aching pain or discomfort is lessened through changing pushing directions in parallel to the skin while pushing the skin over the first sheet member affixed in the second step; a fourth step of affixing the backside surface of the one end portion of the second sheet member to the first front side surface of the first sheet member so that the other end portion of the second sheet member where the first sheet member is not attached is aligned with the direction detected in the third step; and a fifth step of affixing the backside surface of the second sheet member to the skin after the other end portion of the second sheet member is stretched and extended in the longitudinal direction.

According to a tenth aspect of the present invention, in the method of alleviating an aching pain described above, it is preferred that a reinforcement sheet is detachably attached to a second front side surface of the second sheet member substantially over a longitudinal direction thereof. The reinforcement sheet is formed of a material having a flexural strength greater than that of the second sheet member. Further, the reinforcement sheet is formed of a non-stretchable material, and is divided with a dividing line crossing the longitudinal direction thereof. In this case, in the fifth step, it is determine an elongation of the second sheet member according to a distance between the reinforcement sheets divided and attached to the second sheet member. After the second sheet member is affixed to the skin, the reinforcement sheets are removed from the second sheet member.

According to an eleventh aspect of the present invention, in the method of alleviating an aching pain described above, it is preferred that a release sheet member is detachably attached to the first backside surface and the second backside surface with the adhesive compound applied thereto, so that the release sheet member covers the portion and detachably attached to the adhesive compound.

According to a twelfth aspect of the present invention, in the method of alleviating an aching pain described above, when the release sheet member is divided with the dividing line crossing the longitudinal direction thereof at the other end portion of the second sheet member, to which the first sheet member is not fixed, in the fourth step of affixing the second sheet member, the second sheet is used, in which only the release sheet member at the one end portion is removed, and the lease sheet member at the other end portion remains. In this case, in the fifth step, the backside surface of the second sheet member without the release sheet member is affixed to the skin after the release sheet member and the other end portion of the second sheet member are stretched and extended with a finger in the longitudinal direction. Afterward, the release sheet member at the other end portion is removed, so that the backside surface of the second sheet member at the other end portion is affixed to the skin.

According to a thirteenth aspect of the present invention, the method of alleviating an aching pain described above may further include a last step of rubbing the second sheet member more than one time from the one end portion thereof toward the other end portion thereof while pressing the first sheet member.

According to the present invention having the configuration described above, it is possible to obtain the following effects. When the skin stretching tape is applied to the skin, after the first sheet member is attached to the skin, the second sheet member is stretched and attached to the skin. As a result, the area where the first sheet member is attached is stretched in the direction that the second sheet member is extended. It is found that, when a skin above an area where a muscle causes a tension is stretched in a specific direction, it is possible to alleviate the aching pain in the muscle. Accordingly, after the first sheet member is attached to the area where the muscle causes a tension, when the second sheet member is stretched and attached to the area in the direction that alleviates the aching pain in the muscle, it is possible to maintain the area where the muscle causes a tension in the state that is extended in the direction that alleviates the aching pain in the muscle.

According to the present invention having the configuration described above, the first sheet member is formed of the non-stretchable material. As a result, the area where the first sheet member is attached is stretched as a whole by the second sheet member. Accordingly, it is possible to uniformly stretch the skin above the area where the muscle causes a tension.

According to the present invention having the configuration described above, when the first sheet member is formed in the circular shape, it is possible to stretch a range away by an equal distance from the area where the muscle causes a tension as a center point with the second sheet member. Further, when the first sheet member is formed in a shape having contact points with a circle that forms a polygonal shape when the shape is fitted in the circle, it is possible to prevent a signal transmitted to a brain through the skin from being too complicated. Further, it is possible to prevent the patient from getting used to the stimulus that alleviates the pain or the tension.

According to the present invention having the configuration described above, when the second portion has the length in the longitudinal direction thereof three times to five times of that of the first sheet member, it is possible to obtain a sufficient tension and easy handling.

According to the present invention having the configuration described above, when the second portion has the width in the direction perpendicular to the longitudinal direction smaller than that of the first sheet member, it is possible to apply a force more strongly toward a center side in the area where the muscle causes a tension. Further, when the skin stretching tape has the outer circumferential edge having no corner portion smaller than 180 degrees, it is possible to effectively prevent the first sheet member and the second sheet member from being peeled off from the corner portion. Further, when the skin stretching tape includes the release sheet member detachably attached to the first backside surface and the second backside surface, it is possible to prevent the skin stretching tape from sticking to other article when the skin stretching tape is transported or stored. As a result, when the skin stretching tape is in an actual use, it is possible to easily use the skin stretching tape after removing the release sheet member.

According to the present invention having the configuration described above, when the skin stretching tape includes the first sheet member and the second sheet member separated from the first sheet member in advance, it is possible to affix the first sheet member without considering the direction thereof after the skin is pushed with a finger so that the location of the muscle where the large tension occurs is detected. Afterward, the second sheet member is fixed to the skin in the specific direction where the first sheet member is affixed after detecting the direction in which the tension of the muscle is lessened.

Accordingly, as compared with the skin stretching tape in which the first sheet member and the second sheet member are integrated in advance, it is possible to operate in order, and to accurately affix the skin stretching tape at the specific location in the specific direction.

According to the present invention having the configuration described above, when the reinforcement sheet is attached to the front side surface of the second sheet member, it is difficult to bend the second sheet member. Accordingly, it is possible to the backside surface of the second sheet member with the adhesive compound applied thereto from being stuck each other before the second sheet member is affixed to the first sheet member or the skin.

According to the present invention having the configuration described above, when the reinforcement sheet is formed of a non-stretchable material, and is divided with the dividing line crossing the longitudinal direction thereof, it is possible to stretch the second sheet member at the location where the reinforcement sheet is divided when the second sheet member is stretched while the reinforcement sheet is attached to the front side surface of the second sheet member. Accordingly, the reinforcement sheet is stretched such that the divided portions thereof are separated from each other. As a result, it is possible to determine a degree of stretching the second sheet member through visually confirming a distance between the divided portions of the reinforcement sheet.

According to the present invention having the configuration described above, when the one end portion of the second sheet member, to which the first sheet member is fixed, is formed of a transparent material or a semi-transparent material, it is possible to affix the first sheet member while visually confirming the first sheet member when the first sheet member is fixed to the one end portion of the second sheet member. Accordingly, it is possible to easily fix the first sheet member at the proper location on the one end portion of the second sheet member.

According to the present invention having the configuration described above, when the release sheet member is disposed at the portion of the second sheet member with the adhesive compound applied thereto, and the release sheet member is divided with the dividing line crossing the longitudinal direction thereof at the other end portion of the second sheet member, to which the first sheet member is not fixed, it is possible to remove the second sheet member from the release sheet without sticking the adhesive compound of the second sheet member to the finger through holding the portion of the second sheet member with the finger while the release sheet member remains on the other end portion. Further, it is possible to stretch the second sheet member toward the other end portion while holding the second sheet member with the finger after the one end portion of the second sheet member is affixed to the first sheet member.

According to the present invention, in the method of alleviating the aching pain, the first sheet member is attached to the area where the muscle causes a tension. Further, with the second sheet member, it is possible to maintain the area where the muscle causes a tension in the state that is extended in the direction that alleviates the aching pain in the muscle. Accordingly, it is possible to moderate the tension in the muscle at the specific area through tending only the specific area, and to alleviate the aching pain in the muscle. Further, when the skin stretching tape is attached to the skin, it is possible to maintain the effect for a prolonged period of time.

According to the present invention, in the method of alleviating the aching pain, the skin stretching tape is formed of the first sheet member and the second sheet member separated from the first sheet member in advance. After the first sheet member is affixed to the skin, the second sheet member is affixed to the skin. Accordingly, it is possible to affix the second sheet member while confirming the location where the second sheet member is affixed through pushing the skin. Further, it is possible to affix the first sheet member in any direction, so that it is possible to securely affix the first sheet member at any location. Further, the first sheet member is affixed to the skin first. Accordingly, when the second sheet member is affixed to the skin, it is possible to properly affix the second sheet member to the skin simply through remembering the direction in which the first sheet member is affixed.

According to the present invention, when the method further includes the step of rubbing the second sheet member more than one time after the second sheet member is attached to the skin, it is possible to firmly apply and attach the second sheet member to the skin.

BRIEF DESCRIPTION OF THE DRAWINGS

FIG. 1(b) is a schematic exploded perspective view showing the skin stretching tape viewed from the backside thereof;

FIGS. 2(a) and 2(b) are schematic views showing the skin stretching tape according to the first embodiment of the present invention, wherein FIG. 2(a) is a schematic plan view showing the skin stretching tape without a release sheet member thereof, and FIG. 2(b) is a schematic backside view showing the skin stretching tape without the release sheet member thereof;

FIGS. 5(a) and 5(b) are schematic views showing a skin stretching tape according to a second embodiment of the present invention, wherein FIG. 5(a) is a schematic plan view showing the skin stretching tape without a release sheet member thereof, and FIG. 5(b) is a schematic backside view showing the skin stretching tape without the release sheet member thereof;

FIGS. 6(a) and 6(b) are schematic views showing a skin stretching tape according to a third embodiment of the present invention, wherein FIG. 6(a) is a schematic plan view showing the skin stretching tape without a release sheet member thereof, and FIG. 6(b) is a schematic backside view showing the skin stretching tape without the release sheet member thereof;

FIGS. 7(a) and 7(b) are schematic views showing a skin stretching tape according to a fourth embodiment of the present invention, wherein FIG. 7(a) is a schematic perspective view showing a first adhesive tape of the skin stretching tape viewed from a front side thereof, and FIG. 7(b) is a schematic exploded perspective view showing the first adhesive tape of the skin stretching tape viewed from the front side thereof;

FIGS. 8(a) and 8(b) are schematic views showing the skin stretching tape according to the fourth embodiment of the present invention, wherein FIG. 8(a) is a schematic perspective view showing a second adhesive tape of the skin stretching tape viewed from a front side thereof, and FIG. 8(b) is a schematic exploded perspective view showing the second adhesive tape of the skin stretching tape viewed from the front side thereof;

DETAILED DESCRIPTION OF THE PREFERRED EMBODIMENTS

Hereunder, embodiments of the present invention will be explained with reference to the accompanying drawings.

First Embodiment

Figure 1:
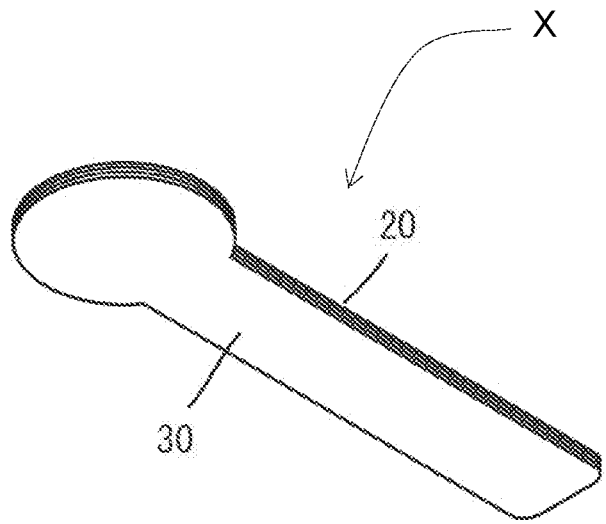
FIGS. 1(*a*) and 1(*b*) are schematic views showing a skin stretching tape according to a first embodiment of the present invention, wherein FIG. 1(*a*) is a schematic perspective view showing the skin stretching tape viewed from a backside thereof.
Figure 1:
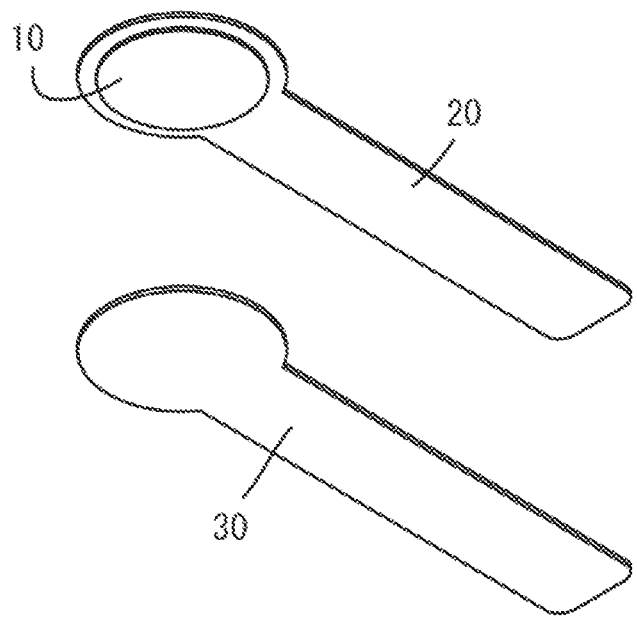

A first embodiment of the present invention will be explained. FIGS. 1(a) and 1(b) are schematic views showing a skin stretching tape X according to a first embodiment of the present invention. More specifically, FIG. 1(a) is a schematic perspective view showing the skin stretching tape X viewed from a backside thereof, and FIG. 1(b) is a schematic exploded perspective view showing the skin stretching tape X viewed from the backside thereof.

Figure 2:
Figure 2:

FIGS. 2(a) and 2(b) are schematic views showing the skin stretching tape X according to the first embodiment of the present invention, wherein FIG. 2(a) is a schematic plan view showing the skin stretching tape X without a release sheet member 30 thereof, and FIG. 2(b) is a schematic backside view showing the skin stretching tape without the release sheet member 30 thereof.

As shown in FIG. 1(a), the skin stretching tape X includes a first sheet member 10, a second sheet member 20, and the release sheet member 30.

In the first embodiment, the first sheet member 10 is formed of a thin non-stretch material including a plastic sheet, a metal sheet, and a cloth sheet. Further, the first sheet member 10 is formed in a circular shape. An adhesive compound that is not harmful a human body is applied to a backside surface of the first sheet member 10.

More specifically, the first sheet member 10 is formed in a circular shape having a diameter of about 10 mm, and is formed of a non-stretchable sheet with an adhesive compound applied to one surface thereof. It should be noted that an acupuncture sheet for fixing a short needle stuck below a skin may be used as the first sheet member 10. An example of the material of the first sheet member 10 may include a medical non-stretchable tape or sheet such as ST-204 (a product of Nitto Medical Corporation). When the first sheet member 10 is produced from the medical non-stretchable tape such as ST-204, which is commercially available as a large sheet with the A-4 size, the medical non-stretchable tape is punched out in the circular shape having a specific diameter. It should be noted that the medical non-stretchable tape such as ST-204 has a three-layered structure having a base layer formed of a cloth, an adhesive layer formed of an acrylic compound, and a releasing layer.

Further, the first sheet member 10 may have a circular shape having a different diameter within a range from 6.0 mm to 20.0 mm according to a location of a body where the skin stretching tape X is attached. For example, when the skin stretching tape X is attached to a waist area or a back area of the body, the first sheet member 10 having a diameter between 15.0 and 20.0 mm may be used. Further, when the skin stretching tape X is attached to an upper arm area of a body, the first sheet member 10 having a diameter between 7.0 and 8.0 mm is used. Further, even when the skin stretching tape X is attached to the waist area or the back area of the body, the diameter of the first sheet member 10 may be adjusted according to a whole body size of a patient.

In the first embodiment, a thickness of the first sheet member 10 may be in a range between 0.21 and 0.29 mm according to that of a commercial product of the medical non-stretchable tape. It should be noted that when the first sheet member 10 has the thickness slightly larger than the range between 0.21 and 0.29 mm as a whole or at least a center portion thereof within a diameter about 3.0 to 5.0 mm, it may be possible to obtain a pressing stimulus and improve the effectiveness of the treatment.

In the first embodiment, the second sheet member 20 is an elongated band shaped sheet formed of a stretchable material including a cloth sheet and an elastomer sheet. The second sheet member 20 has one end portion enlarged in a circular shape having a diameter slightly larger than that of the first sheet member 10. Further, a front surface of the first sheet member 10 is attached and fixed to a backside surface of the one end portion of the second sheet member 20 thus enlarged in the circular shape. An adhesive compound that is not harmful a human body is applied to a backside surface of the second sheet member 20 other than an area where the first sheet member 10 is attached.

In the first embodiment, the second sheet member 20 further has the other end portion where the first sheet member 10 is not attached. The other end portion of the second sheet member 20 has corner portions curved in an R shape, so that it is difficult to peel off the skin stretching tape X when the skin stretching tape X is affixed to a skin. An extended portion of the second sheet member 20 other than the enlarged circular portion thereof has a width three quarters to a half of the diameter of the first sheet member 10. Further, the second sheet member 20 has a length three to five times of the diameter of the first sheet member 10.

More specifically, in the first embodiment, the second sheet member 20 may include a stretchable tape for supporting a muscle through a skin or a stretchable bandage. The stretchable tape may include Kinesiology Tape EX (a product of NITTO MEDICAL CORPORATION), and the stretchable bandage may include Kinesiology Soft (a product of NITTO MEDICAL CORPORATION). It should be noted that Kinesiology Tape EX is stretchable both in a longitudinal direction and a lateral direction, and Kinesiology Soft is stretchable only in a longitudinal direction (an extension direction). The stretchable tape may be formed of a cloth and an acrylic adhesive compound containing natural rubber is applied to the backside of the cloth.

In the first embodiment, similar to the first sheet member 10, the second sheet member 20 may have a different shape having a different size according to the location of the body where the skin stretching tape X is attached. For example, when the first sheet member 10 has the diameter of 10.0 mm, the second sheet member 20 may have a width of 15.0 mm and a length of 40.0 mm, or a width of 12.5 mm and a length of 35 mm. Further, when the first sheet member 10 has the diameter of 15.0 mm, the second sheet member 20 may have a width in a range between 18.0 and 20.0 mm and a length in a range between 45.0 and 50.0 mm.

In the first embodiment, the second sheet member 20 may have a length greater than 50.0 mm. However, when it is necessary to attach the skin stretching tape X at a plurality of locations near one affected area of the patient, it may be difficult if the second sheet member 20 has a length greater than 50.0 mm. For example, when a patient has the aching pain at a plurality of locations situated nearby, for example, in a surface layer, an intermediate layer, and a deep layer of a skin thereof, there may be a case where the aching pain is realized at a new location when the aching pain at one of the locations is alleviated. In such a case, it is necessary to attach the skin stretching tape X at a plurality of locations in different directions. When the skin stretching tape X is attached at a plurality of locations, the second sheet member 20 may be overlapped with each other. Accordingly, it is preferred that the second sheet member 20 has a length in a range between 45.0 and 50.0 mm.

In the first embodiment, in consideration of skin rash and skin irritation, it is preferred that a product of a company with established reputation in the medical field is used as a material of the first sheet member 10 and the sheet member 30. In particular, the material of the first sheet member 10 may include a synthetic resin film such as a polyvinyl chloride film and a polyolefin film (more preferably, a film material used for a medical application); a non-stretchable natural fiber fabric such as cotton fabric; and a non-stretchable synthetic fiber fabric. Further, the material of the second sheet member 20 may include a stretchable natural fiber fabric such as cotton fabric (more preferably, a co-woven fabric of cotton and polyurethane); an elastomer sheet or an elastomer fiber fabric formed of natural rubber and the like; and a stretchable synthetic fiber fabric such as a polyurethane non-woven fabric.

In the first embodiment, the sheet member 30 has an outer shape similar to that of the second sheet member 20, and is attached to the backside surfaces of the first sheet member 10 and the second sheet member 20 with the adhesive compound applied thereto. Further, the sheet member 30 is formed of a paper sheet with a smooth processed surface, so that the sheet member 30 is easily peeled off from the first sheet member 10 and the second sheet member 20 with the adhesive compound applied thereto.

Figure 3:
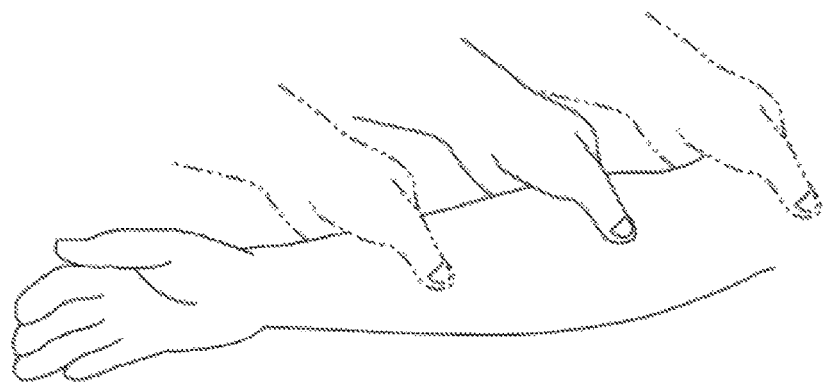
FIGS. 3(a) to 3(c) are schematic views showing a first step to a third step of a method of alleviating an aching pain according to the first embodiment of the present invention.
Figure 3:
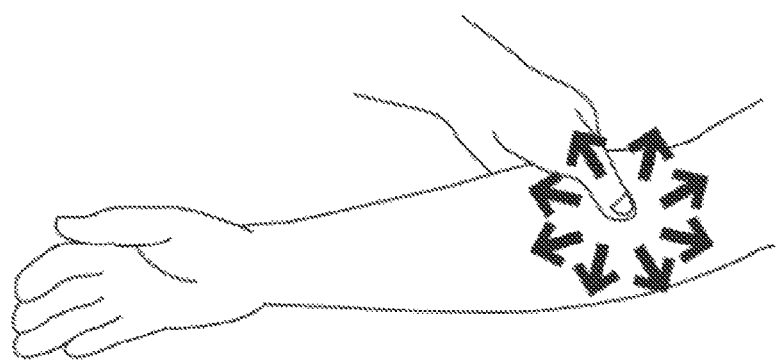
Figure 3:
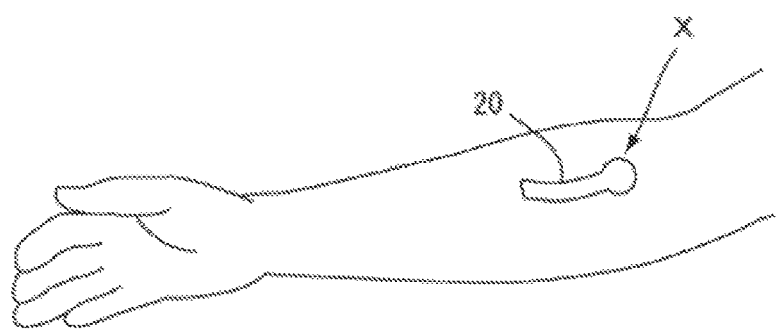
Figure 4:
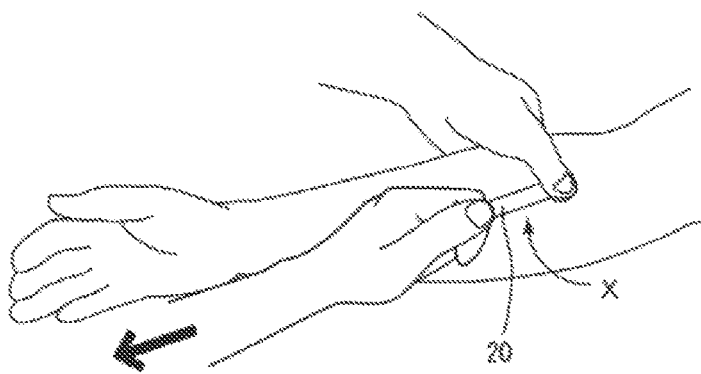
FIGS. 4(a) to 4(c) are schematic views showing a fourth step to a fifth step of the method of alleviating the aching pain according to the first embodiment of the present invention.
Figure 4:
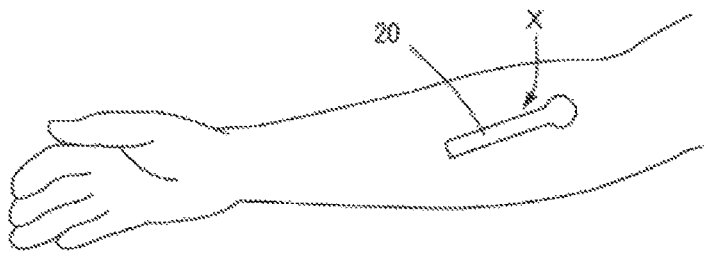
Figure 4:
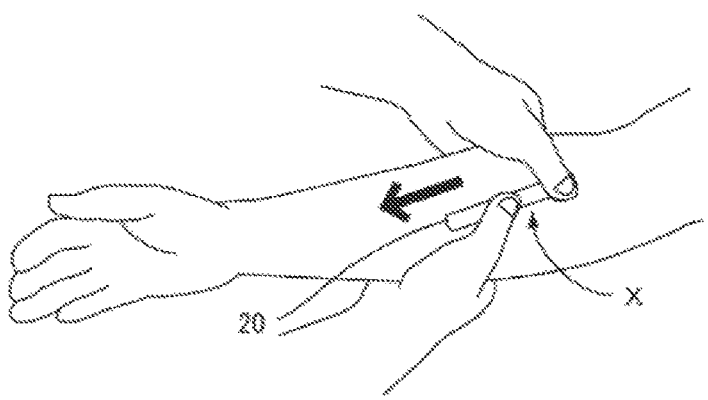

An operation of a method of alleviating the aching pain will be explained with reference to FIGS. 3(a)-3(c) to 4(a)-4(c). FIGS. 3(a) to 3(c) are schematic views showing a first step to a third step of the method of alleviating an aching pain according to the first embodiment of the present invention. FIGS. 4(a) to 4(c) are schematic views showing a fourth step to a fifth step of the method of alleviating the aching pain according to the first embodiment of the present invention.

In the first step, as shown in FIG. 3(a), a practitioner pushes the skin of the patient with a finger while changing a pushing location, so that the practitioner detects a location of the muscle of the patient where the patient feels the aching pain and/or discomfort. It should be noted that the location of the muscle where the patient feels the aching pain and/or the discomfort corresponds to the location of the muscle where a large tension occurs.

In the second step, after the practitioner detects the location of the muscle of the patient where the large tension occurs in the first step, as shown in FIG. 3(b), the practitioner detects a direction in which the aching pain or discomfort is lessened through changing pushing directions in parallel to the skin while pushing the skin at the location of the muscle, where the large tension occurs, detected in the first step. It should be noted that the direction detected in the second step corresponds to a direction that the large tension in the muscle is alleviated.

In the third step, after the practitioner detects the direction that the large tension in the muscle is alleviated in the second step, as shown in FIG. 3(c), the practitioner peels off the sheet member 30 from the skin stretching tape X, and affixes the first sheet member 10 to the skin of the patient at the location of the muscle of the patient where the large tension occurs in the first step, so that the other end portion of the second sheet member 20 where the first sheet member 10 is not attached is aligned with the direction that the large tension in the muscle is alleviated detected in the second step.

In the fourth step, as shown in FIG. 4(a), the practitioner stretches and extends the other end portion of the second sheet member 20 in the longitudinal direction, that is, the direction that the large tension in the muscle is alleviated. Then, as shown in FIG. 4(b), the practitioner affixes the second sheet member 20 to the skin of the patient. It should be noted that when the practitioner stretches the second sheet member 20, the practitioner pushes and holds the first sheet member 10 with the finger.

In the fifth step, as shown in FIG. 4(c), the practitioner rubs the second sheet member 20 more than one time from the one end portion thereof toward the other end portion thereof in the direction that the large tension in the muscle is alleviated while the practitioner is pressing the first sheet member 10, so that an entire portion of the second sheet member 20 is firmly attached and aligned to the skin of the patient. Through the process described above, the method of alleviating the aching pain at one location is completed.

In the first embodiment, when there is a plurality of locations in the muscle where the patient feels the large tension, the method of alleviating the aching pain described above may be performed at each of the locations, so that the large tension at each of the locations is alleviated. When the large tension in the muscle is alleviated, it is possible to alleviate the aching pain.

As described above, in the method of alleviating the aching pain in the first embodiment, the skin stretching tape X is used to alleviate the large tension in the muscle. Accordingly, it is possible to maintain the relax state in the muscle for a prolonged period of time. Further, it is possible to easily treat the aching pain.

Second Embodiment

Figure 5:
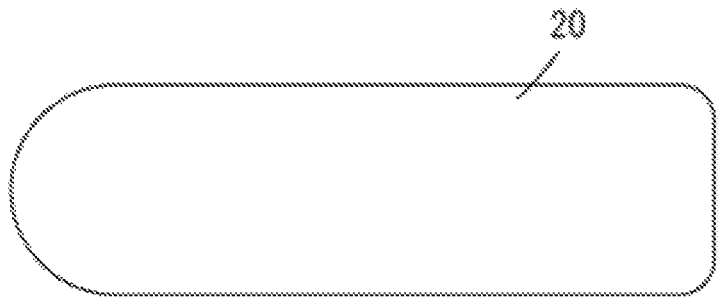
Figure 5:
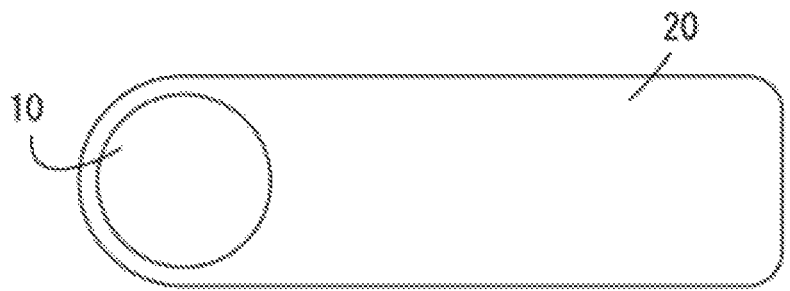

A second embodiment of the present invention will be explained next with reference to FIGS. 5(a) and 5(b). FIGS. 5(a) and 5(b) are schematic views showing a skin stretching tape according to the second embodiment of the present invention. More specifically, FIG. 5(a) is a schematic plan view showing the skin stretching tape without the release sheet member 30 thereof, and FIG. 5(b) is a schematic backside view showing the skin stretching tape without the release sheet member 30 thereof.

As described above, in the first embodiment, the second sheet member 20 has the one end portion having the circular shape and the extended portion having the band shape with the width smaller than the diameter of the circular shape. In the second embodiment, as shown in FIGS. 5(a) and 5(b), the extended portion of the second sheet member 20 has a width equal to the diameter of the circular shape. Other configuration and the materials of the first sheet member 10 and the second sheet member 20 are similar to those in the first embodiment.

Third Embodiment

Figure 6:
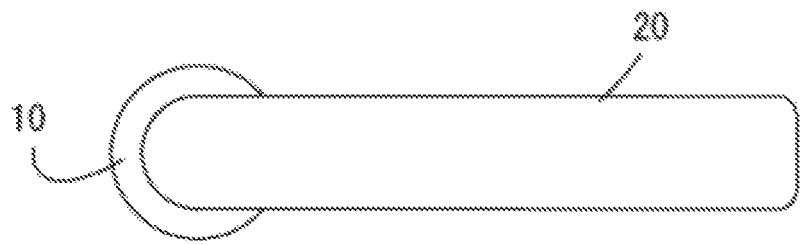
Figure 6:
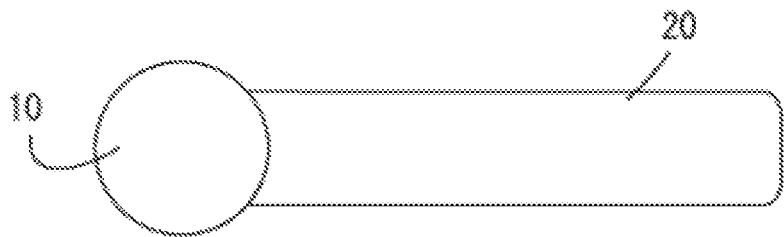

A third embodiment of the present invention will be explained next with reference to FIGS. 6(a) and 6(b). FIGS. 6(a) and 6(b) are schematic views showing a skin stretching tape according to the third embodiment of the present invention. More specifically, FIG. 6(a) is a schematic plan view showing the skin stretching tape without the release sheet member 30 thereof, and FIG. 6(b) is a schematic backside view showing the skin stretching tape without the release sheet member 30 thereof.

As shown in FIGS. 6(a) and 6(b), in the third embodiment, the second sheet member 20 is entirely formed in a band shape, and does not have the one end portion having the circular shape. Further, the first sheet member 10 has the circular shape having the diameter greater than a width of the second sheet member 20. IN the third embodiment, the first sheet member 10 is attached to one end portion of the second sheet member 20, so that a part of the front surface of the first sheet member 10 is exposed from the second sheet member 20.

Fourth Embodiment

A fourth embodiment of the present invention will be explained next with reference to the accompanying drawings. In the fourth embodiment, a skin stretching tape is formed of two types of adhesive tapes.

Figure 7:
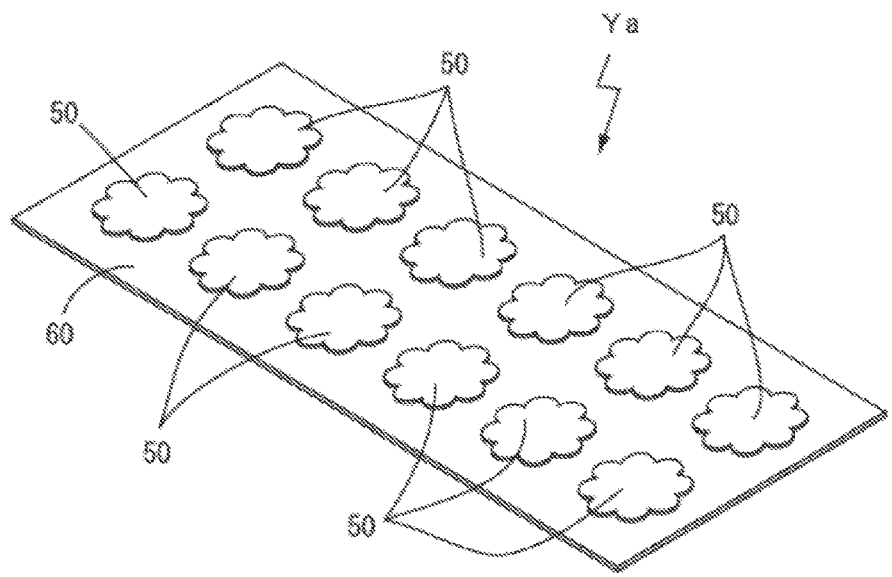
Figure 7:
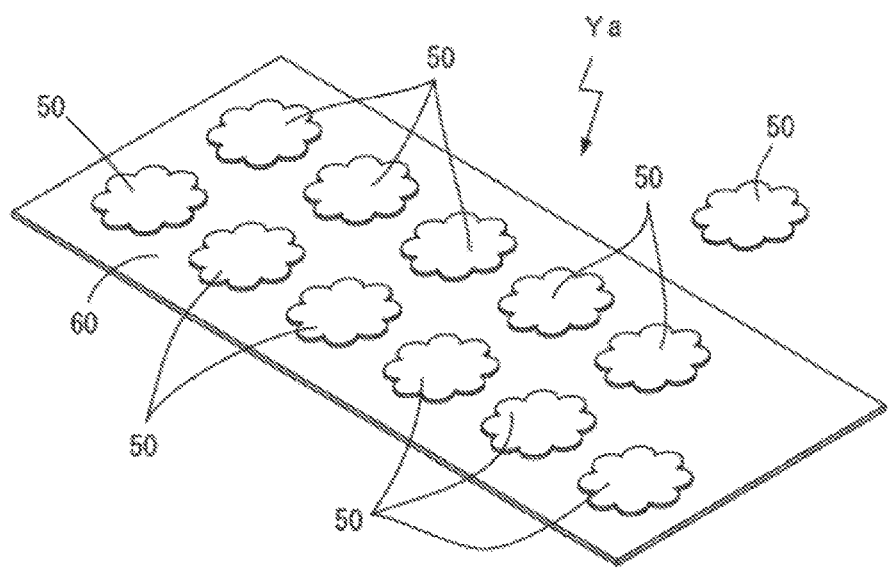

FIGS. 7(a) and 7(b) are schematic views showing the skin stretching tape according to the fourth embodiment of the present invention. More specifically, FIG. 7(a) is a schematic perspective view showing a first adhesive tape Ya of the skin stretching tape viewed from a front side thereof, and FIG. 7(b) is a schematic exploded perspective view showing the first adhesive tape Ya of the skin stretching tape viewed from the front side thereof.

As shown in FIGS. 7(a) and 7(b), the first adhesive tape Ya includes first sheet members 50 and a release sheet member 60. It should be noted that the first adhesive tape Ya includes twelve of the first sheet members 50 disposed on the release sheet member 60 as a common sheet member having a large rectangular shape.

In the fourth embodiment, each of the first sheet members 50 is formed of a material similar to that of the first sheet member 10 in the first embodiment, and a similar adhesive compound is applied to a backside surface thereof. Further, each of the first sheet members 50 is formed in a shape resembling a flower pattern in a plan view having contact points with a circle that forms a polygonal shape when the shape is fitted in the circle. The release sheet member 60 is formed of a paper sheet member having a the rectangular shape, and a front side surface thereof is processed to be smooth such that each of the first sheet members 50 with the adhesive compound applied thereon can be easily removed. When twelve of the first sheet members 50 are attached to the release sheet member 60 through the adhesive compound applied on the backside surface of each of the first sheet members 50, the release sheet member 60 holds the first sheet members 50.

Figure 8:
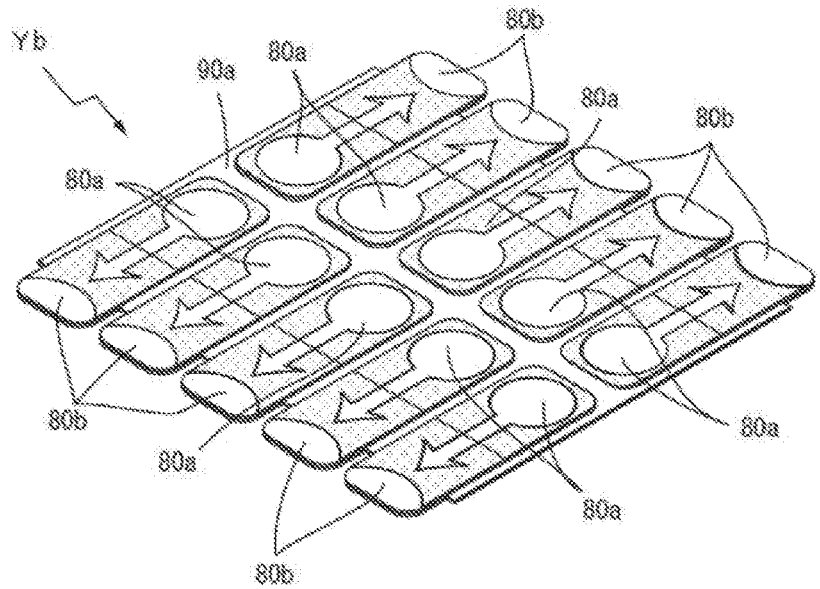
Figure 8:
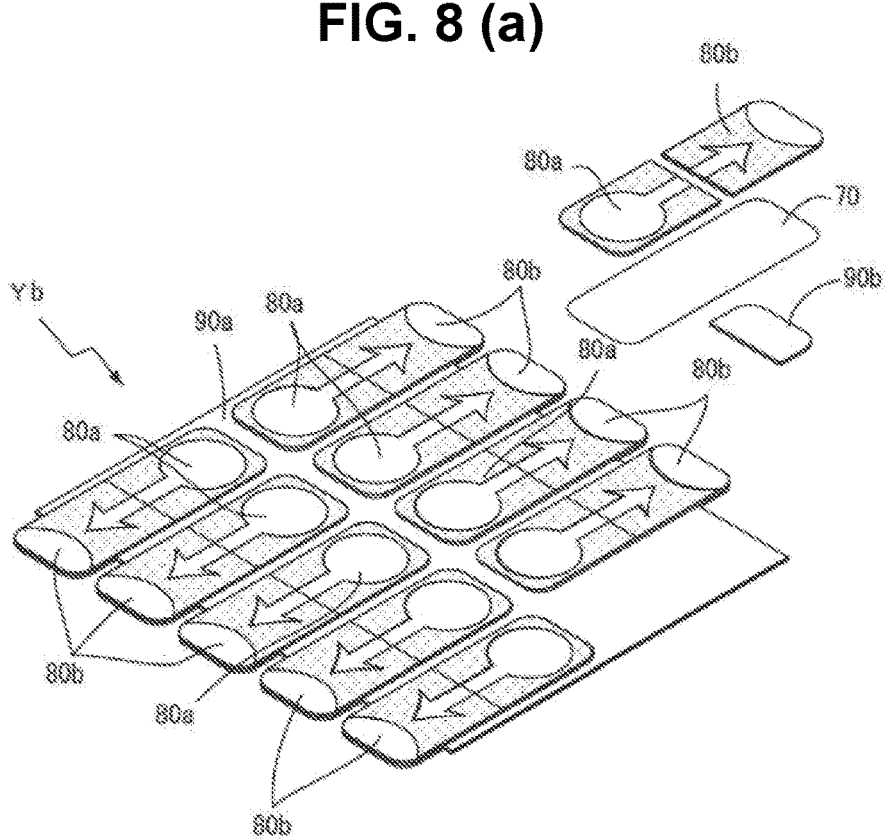

FIGS. 8(a) and 8(b) are schematic views showing the skin stretching tape according to the fourth embodiment of the present invention. More specifically, FIG. 8(a) is a schematic perspective view showing a second adhesive tape Yb of the skin stretching tape viewed from a front side thereof, and FIG. 8(b) is a schematic exploded perspective view showing the second adhesive tape Yb of the skin stretching tape viewed from the front side thereof.

As shown in FIGS. 8(a) and 8(b), the second adhesive tape Yb includes second sheet members 70; reinforcement sheet members 80a; reinforcement sheet members 80b; a release sheet member 90a; and release sheet members 90b. It should be noted that the second adhesive tape Yb includes twelve of the second sheet members 70, the reinforcement sheet members 80a, the reinforcement sheet members 80b, and the release sheet members 90b disposed on the release sheet member 90a as a common sheet member having a large rectangular shape.

In the fourth embodiment, each of the second sheet members 70 is formed of a stretchable material similar to that of the second sheet member 20 in the first embodiment, and is formed of a transparent or semi-transparent elastomer. Further, each of the second sheet members 70 is formed in a rectangular shape in a plan view having four corner portions curved in an R shape.

In the fourth embodiment, each of the reinforcement sheet members 80a and 80b is a sheet member formed of a non-stretchable transparent material such as a synthetic plastic that is more rigid than the second sheet members 70. Further, each of the reinforcement sheet members 80a and 80b is formed in a shape in a plan view similar to that of the second sheet members 70, and is divided into two portions at a center thereof in a longitudinal direction thereof. An adhesive compound with a weak adhesion force is applied to backside surfaces of the reinforcement sheet members 80a and 80b, so that the reinforcement sheet members 80a and 80b are fixed to the second sheet members 70 while being completely overlapped. Accordingly, it is possible to remove the reinforcement sheet members 80a and 80b from the second sheet members 70 with a weak force.

In the fourth embodiment, the reinforcement sheet members 80a and 80b have surfaces printed in a specific pattern. In the specific pattern, there are a circular window, an arrow, and a specific area all in transparent. The circular window is situated at a location corresponding to one end portion of each of the second sheet members 70. The arrow is situated at a middle portion thereof to point from the circular window toward the other end portion of each of the second sheet members 70. The certain area is situated at the other end portion of each of the second sheet members 70.

In the fourth embodiment, the release sheet member 90a is formed of a paper sheet member having a rectangular shape with a sufficient size, so that ten of the second sheet members 70 can be attached to the release sheet member 90a except the other end portions of the second sheet members 70. Further, a front side surface of the release sheet member 90a is processed to be smooth such that each of the second sheet members 70 with the adhesive compound applied thereon can be easily removed. When the second sheet members 70 are attached to the release sheet member 90a through the adhesive compound applied on the backside surface of each of the second sheet members 70, the release sheet member 90a holds the second sheet members 70.

In the fourth embodiment, each of the release sheet members 90b is formed of a paper sheet member having a shape corresponding to that of the other end portion of each of the second sheet members 70 situated outside the release sheet member 90a. Further, a front side surface of each of the release sheet members 90b is processed to be smooth such that each of the second sheet members 70 with the adhesive compound applied thereon can be easily removed. When the other end portions of the second sheet members 70 are attached to the release sheet members 90b through the adhesive compound applied on the backside surface of each of the second sheet members 70, the release sheet members 90b hold the second sheet members 70.

An operation of a method of alleviating the aching pain will be explained with reference to the accompanying drawings. In the method, the skin stretching tape formed of the first adhesive tape Ya and the second adhesive tape Yb is used to alleviate the tension in the muscle, so that the aching pain at a specific location is alleviated.

Figure 9:
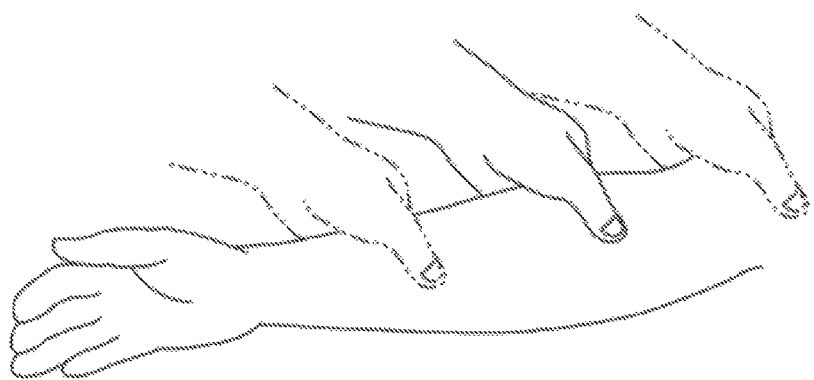
FIGS. 9(a) to 9(c) are schematic views showing a first step to a third step of a method of alleviating an aching pain according to the fourth embodiment of the present invention.
Figure 9:
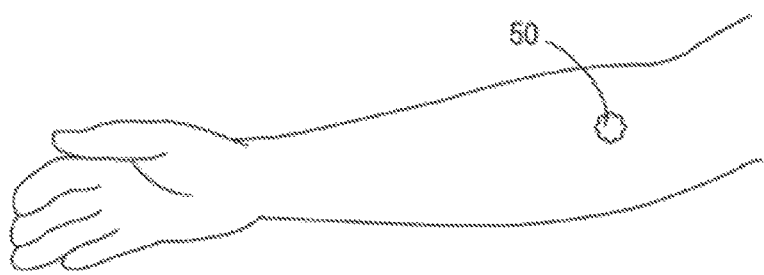
Figure 9:
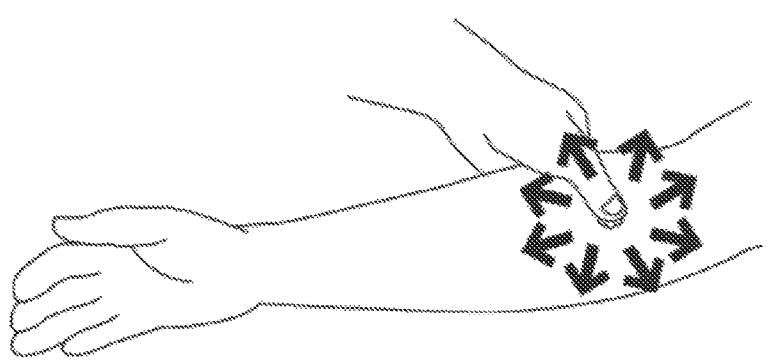
Figure 10:
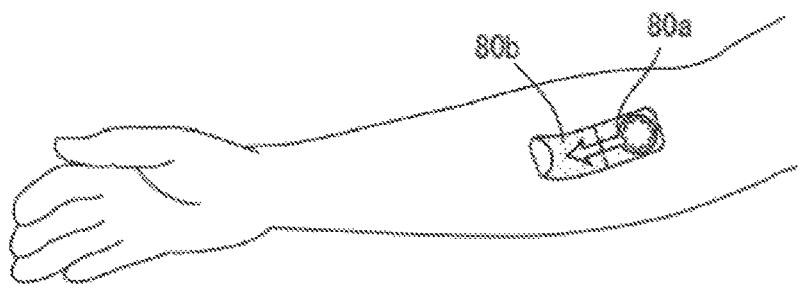
FIGS. 10(a) to 10(c) are schematic views showing a fourth step to a fifth step of the method of alleviating the aching pain according to the fourth embodiment of the present invention.
Figure 10:
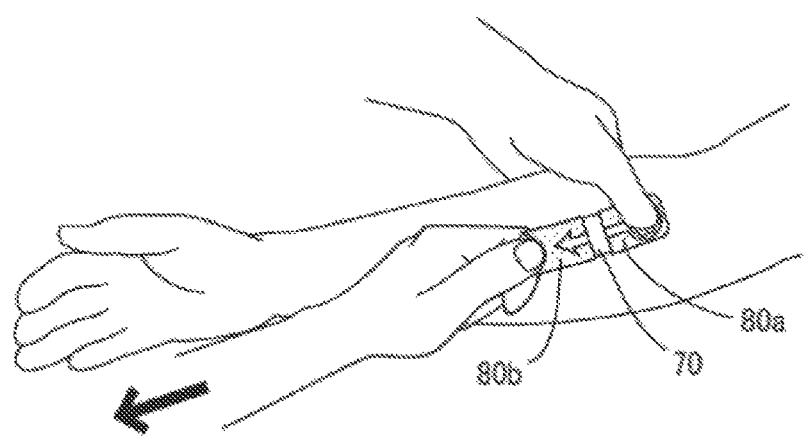
Figure 10:
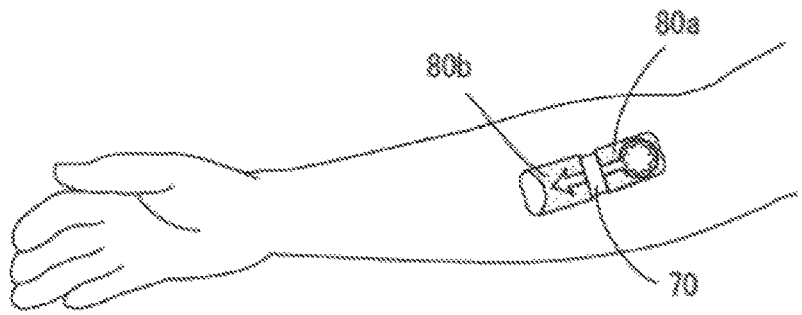

FIGS. 9(a) to 9(c) are schematic views showing a first step to a third step of the method of alleviating the aching pain according to the fourth embodiment of the present invention. FIGS. 10(a) to 10(c) are schematic views showing a fourth step to a fifth step of the method of alleviating the aching pain according to the fourth embodiment of the present invention.

In the first step, as shown in FIG. 9(a), a practitioner pushes the skin of the patient with a finger while changing a pushing location, so that the practitioner detects a location of the muscle of the patient where the patient feels the aching pain and/or discomfort. It should be noted that the location of the muscle where the patient feels the aching pain and/or the discomfort corresponds to the location of the muscle where a large tension occurs.

In the second step, after the practitioner detects the location of the muscle of the patient where the large tension occurs in the first step, as shown in FIG. 9(b), the practitioner removes the first sheet members 50 from the first adhesive tape Ya, and affixes the first sheet members 50 to the location of the muscle of the patient where the large tension occurs.

In the third step, as shown in FIG. 9(c), the practitioner detects a direction in which the aching pain or discomfort is lessened or disappeared through changing pushing directions in parallel to the skin while pushing the skin at the location of the muscle through the first sheet members 50 with the finger. It should be noted that the direction detected in the third step corresponds to a direction that the large tension in the muscle is alleviated.

After the practitioner detects the direction in which the tension is alleviated in the third step, in the fourth step, as shown in FIG. 10(a), the practitioner peels off the second adhesive tape Yb from the release sheet member 90a, and affixes the backside surface of the second sheet member 70 at the one end portion thereof to the surface of the first sheet member 50. At this time, the other end portion of the second sheet member 70 is aligned with the direction in which the tension is alleviated. More specifically, the arrow printed on the reinforcement sheet member 80a and the reinforcement sheet member 80b is aligned with the direction in which the tension is alleviated. Further, the first sheet member 50 that is affixed in the second step is accommodated in the circle window of the reinforcement sheet member 80a situated at the one end portion of the second sheet member 70.

In the fifth step, as shown in FIG. 10(b), the practitioner holds and stretches the release sheet member 90a and the other end portion of the second sheet member 70 in the longitudinal direction, that is, the direction that the large tension in the muscle is alleviated. When the practitioner holds and stretches the second sheet member 70, the practitioner holds the one end portion of the second sheet member 70 with the finger where the first sheet member 50 is affixed.

Figure 11:
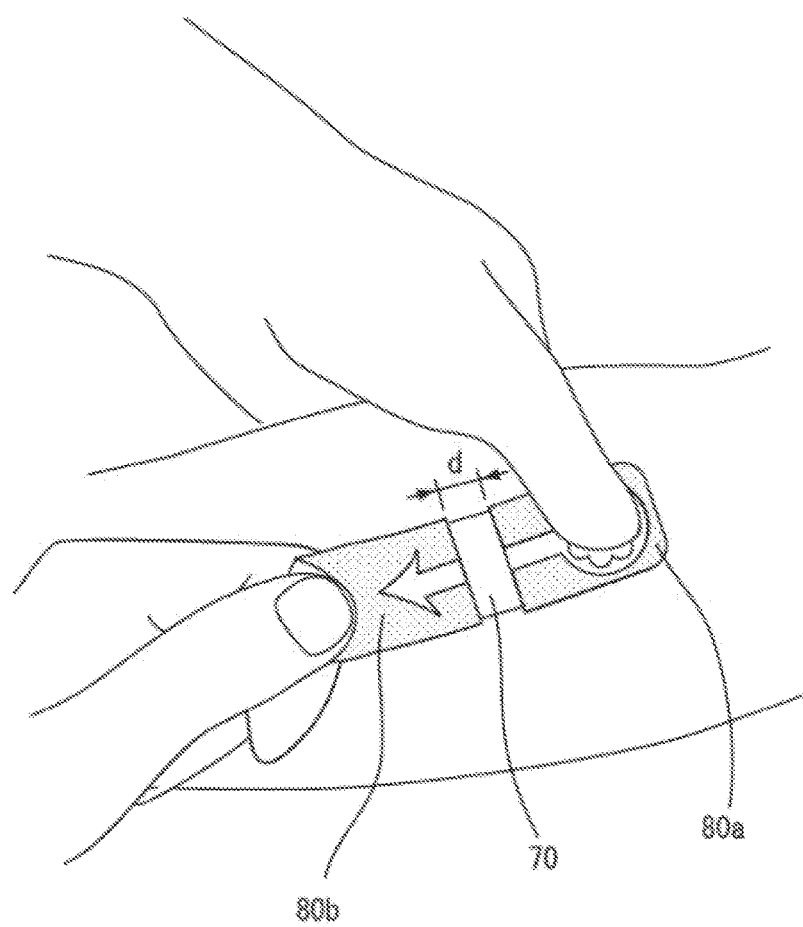
FIG. 11 is an enlarged view showing the fifth step of the method of alleviating the aching pain according to the fourth embodiment of the present invention.

FIG. 11 is an enlarged view showing the fifth step of the method of alleviating the aching pain according to the fourth embodiment of the present invention.

As described above, the reinforcement sheet members 80a and the reinforcement sheet members 80b formed of the non-stretchable material are attached to the surface of the second sheet member 70, so that the portion of the second sheet member 70 where the reinforcement sheet member 80a and the reinforcement sheet member 80b are attached is hardly stretched. Accordingly, at shown in FIG. 11, when the practitioner stretches the second sheet member 70, only the portion of the second sheet member 70 between the reinforcement sheet member 80a and the reinforcement sheet member 80b is stretched. As a result, the distance d between the reinforcement sheet member 80a and the reinforcement sheet member 80b is extended. It should be noted that, when the distance d between the reinforcement sheet member 80a and the reinforcement sheet member 80b reaches a specific level, for example, 5 mm, it is determined that the practitioner stretches the second sheet member 70 to a proper extent.

Then, as shown in FIG. 10(c), the practitioner affixes the portion of the second sheet member 70 other than the one end portion thereof to the skin of the patient while the second sheet member 70 is being stretched. It should be noted that when the release sheet member 90b is attached to the other end portion of the second sheet member 70, so that the other end portion of the second sheet member 70 is not affixed to the skin.

Figure 12:
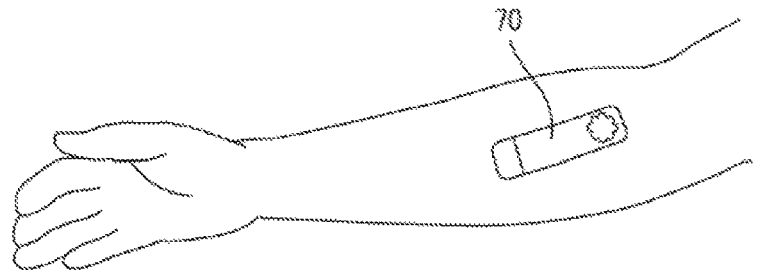
FIGS. 12(a) to 12(c) are schematic views showing the fifth step to a sixth step of the method of alleviating the aching pain according to the fourth embodiment of the present invention.
Figure 12:
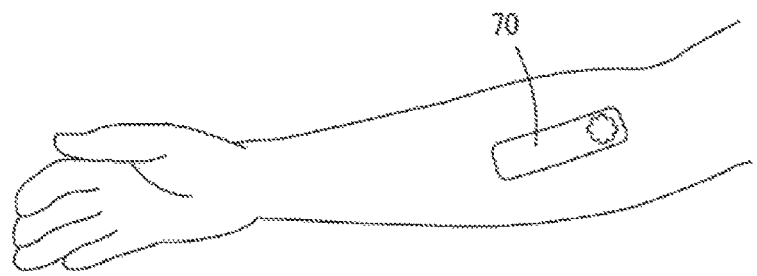
Figure 12:
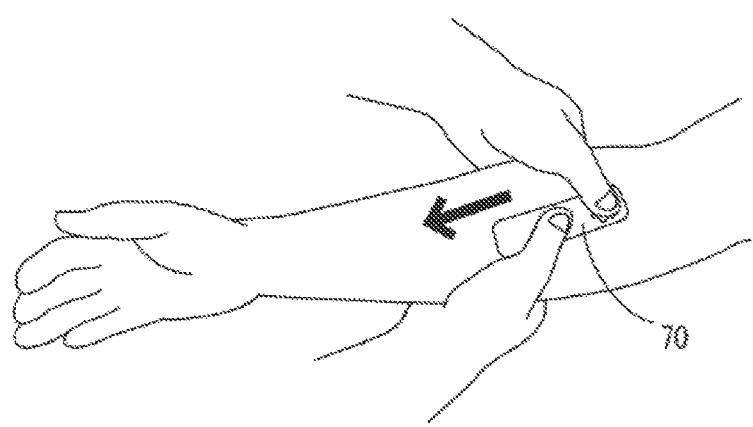

Then, as shown in FIG. 12(a), the practitioner removes the reinforcement sheet member 80a and the reinforcement sheet member 80b from the surface of the second sheet member 70. Afterward, as shown in FIG. 12(b), the practitioner removes the release sheet member 90b from the backside surface of the second sheet member 70 at the one end portion thereof, and the practitioner affixes the other end portion of the second sheet member 70 to the skin.

In the sixth step, as shown in FIG. 12(c), the practitioner rubs the second sheet member 70 several times in the direction that the large tension in the muscle is alleviated while the practitioner is pressing the one end portion of the second sheet member 70 where the first sheet member 50 is attached to, so that an entire portion of the second sheet member 70 is firmly attached and aligned to the skin of the patient. Through the process described above, the method of alleviating the aching pain at one location is completed.

In the fourth embodiment, when there is a plurality of locations in the muscle where the patient feels the large tension, the method of alleviating the aching pain described above may be performed at each of the locations, so that the large tension at each of the locations is alleviated. When the large tension in the muscle is alleviated, it is possible to alleviate the aching pain.

As described above, in the method of alleviating the aching pain in the fourth embodiment, the skin stretching tape is used to alleviate the large tension in the muscle. Accordingly, it is possible to maintain the relax state in the muscle for a prolonged period of time. Further, it is possible to easily treat the aching pain.

Further, in the fourth embodiment, the first sheet members 50 and the second sheet members 70 are separated. Accordingly, it is possible to separately perform the step of affixing the first sheet members 50 after the location where the pain or the discomfort exists is detected, and the step of affixing the second sheet member 70 after the direction to alleviate the pain or the discomfort is detected. As a result, it is possible to simplify the steps. Further, when the second sheet member 70 is affixed to the skin, the first sheet member 50 already indicates the location where the second sheet member 70 is to be affixed, thereby making it possible to securely perform the step.

Further, in the fourth embodiment, the reinforcement sheet member 80a and the reinforcement sheet member 80b are attached to the surface of the second sheet member 70. Accordingly, it is difficult to bend the second sheet member 70, so that it is possible to prevent the surface of the second sheet member 70 with the adhesive compounded allied from being sticking together. Further, when the second sheet member 70 is stretched, it is possible to visually confirm the distance between the reinforcement sheet member 80a and the reinforcement sheet member 80b as the indicator of stretching the second sheet member 70.

Further, in the fourth embodiment, the release sheet member 90b remains at the other end portion of the second sheet member 70. Accordingly, it is possible to keep the finger from the adhesive compound when the practitioner handles the second sheet member 70. In particular, it is possible to easily handle the second sheet member 70 when the practitioner stretches the second sheet member 70.

Further, in the fourth embodiment, the first sheet member 50 has the specific shape in the plan view having the protruding portions along the outer circumference thereof. Accordingly, it is possible to apply a delicate stimulus to the location of the skin where the first sheet member 50 is affixed, thereby improving the effect of alleviating the pain or the discomfort.

Further, in the fourth embodiment, in the first adhesive tape Ya, the first sheet members 50 are disposed on the release sheet member 60 as a common sheet member having a large rectangular shape. Further, in the second adhesive tape Yb, the second sheet members 70, the reinforcement sheet members 80a, the reinforcement sheet members 80b, and the release sheet members 90b are disposed on the release sheet member 90a as a common sheet member having a large rectangular shape. Alternatively, the release sheet member 60 and the release sheet member 90a may be divided corresponding to each of the first sheet members 50 and the second sheet members 70, respectively.

Further, in the first embodiment, the first sheet member 10 is formed in a circular shape, and in the fourth embodiment, the first sheet member 50 is formed in a shape resembling a flower pattern having eight protruding portions. Alternatively, the first sheet member 10 or the first sheet members 50 may be formed in an arbitrary shape. For example, the first sheet members 50 may be formed in a shape having seven or nine protruding portions, or may be formed in a circular shape.

The disclosure of Japanese Patent Application No. 2014-163692, filed on Aug. 11, 2014 is incorporated in the application by reference.

While the invention has been explained with reference to the specific embodiments of the invention, the explanation is illustrative and the invention is limited only by the appended claims.

What is claimed is:

1. A skin stretching tape, comprising:
   a first sheet member formed of a non-stretchable material, and having a first backside surface with a first adhesive compound applied thereto; and
   a second sheet member formed of a stretchable material, and having a second backside surface with a second adhesive compound applied thereto,
   wherein said first sheet member is attached to the second sheet member so that an entire portion of the first sheet member is disposed on the second sheet member,
   said second sheet member has a first portion at one end portion thereof where the first sheet member is attached and a second portion extending to the other end portion thereof where the first sheet member is not attached,
   said first portion has a size larger than that of the first sheet member so that the first portion is exposed around an entire circumference of the first sheet member, and
   said second sheet member has a length in a longitudinal direction thereof greater than twice of that of the first sheet member.

2. The skin stretching tape according to claim 1, wherein said first sheet member has a first circular shape, and
   said first portion has a second circular shape having a diameter greater than that of the first circular shape so that the first portion is exposed around the entire circumference of the first sheet member.

3. The skin stretching tape according to claim 1, wherein said second sheet member has the length in the longitudinal direction thereof three times to five times of that of the first sheet member.

4. The skin stretching tape according to claim 1, wherein said second portion has a width in a direction perpendicular to the longitudinal direction smaller than that of the first sheet member.

5. The skin stretching tape according to claim 4, wherein said second portion has the width one third to a half of that of the first sheet member.

6. The skin stretching tape according to claim 1, wherein said second sheet member has an outer circumferential edge having an angle greater than 180 degrees.

7. The skin stretching tape according to claim 1, further comprising a release sheet member detachably attached to the first backside surface and the second backside surface.

8. The skin stretching tape according to claim 1, further comprising a reinforcement sheet member attached to the second sheet member,
- wherein said reinforcement sheet member has a third backside surface with a third adhesive compound is applied thereto,
- said reinforcement sheet member is configured to be separable into two pieces, and
- said third adhesive compound has an adhesion force weaker than that of the second adhesive compound.

\* \* \* \* \*